(12) United States Patent
Bulent et al.

(10) Patent No.: US 9,750,859 B2
(45) Date of Patent: Sep. 5, 2017

(54) PERMANENT TOTAL ARTIFICIAL HEART DEVICE

(71) Applicants: Oran Bulent, Konya (TR); Oran Omer Faruk, Konya (TR); Avci Elif Oran, Konya (TR)

(72) Inventors: Oran Bulent, Konya (TR); Oran Omer Faruk, Konya (TR); Avci Elif Oran, Konya (TR)

(*) Notice: Subject to any disclaimer, the term of this patent is extended or adjusted under 35 U.S.C. 154(b) by 29 days.

(21) Appl. No.: 14/648,913

(22) PCT Filed: Jan. 10, 2014

(86) PCT No.: PCT/TR2014/000009
§ 371 (c)(1),
(2) Date: Jun. 2, 2015

(87) PCT Pub. No.: WO2014/120101
PCT Pub. Date: Aug. 7, 2014

(65) Prior Publication Data
US 2015/0314054 A1    Nov. 5, 2015

(30) Foreign Application Priority Data

Jan. 29, 2013   (TR) .............................. a 2013 01047

(51) Int. Cl.
*A61M 1/12*   (2006.01)
*A61M 1/10*   (2006.01)

(52) U.S. Cl.
CPC ............ *A61M 1/101* (2013.01); *A61M 1/122* (2014.02); *A61M 1/127* (2013.01); *A61M 1/12* (2013.01);
(Continued)

(58) Field of Classification Search
CPC ...... A61M 1/122; A61M 1/101; A61M 1/127; A61M 2205/8206; A61M 2205/04;
(Continued)

(56) References Cited

U.S. PATENT DOCUMENTS 4,763,032 A * 8/1988 Bramm ................. A61M 1/101
310/90.5
5,613,935 A * 3/1997 Jarvik ................... A61M 1/101
600/16
(Continued)

FOREIGN PATENT DOCUMENTS

TR    2012/00951 A2    9/2012
TR    2012/07222 A2    11/2012
(Continued)

*Primary Examiner* — Paul Prebilic
(74) *Attorney, Agent, or Firm* — Gokalp Bayramoglu (57) ABSTRACT

The invention is about a permanent total artificial heart device that is developed for the patients who are at the end-stage heart failure and included in the heart transplantation program, and which is placed into the ventricles of the patient's heart completely or placed surgically into the space obtained when a piece of ventricle is removed. The device employs "direct drive technology," technically using the advantages of brushless electric motors. Special-designed engines require quite little energy for the pulsatile blood flow produced by stopping and starting synchronously with the ECG signals. It is about a permanent total artificial heart device system that will offer high quality of life for many years to the patients as it protects the heart valves and heart conduction system, has wireless charging and longer battery life.

24 Claims, 6 Drawing Sheets

(52) U.S. Cl.
CPC ............... *A61M 2205/8206* (2013.01); *A61M 2210/125* (2013.01)

(58) Field of Classification Search
CPC .... A61M 2205/103; A61M 2205/3334; A61M 2205/3355; A61M 2205/3351; A61M 2205/3507; A61M 2205/3584; A61M 2210/125
See application file for complete search history.

(56) References Cited

U.S. PATENT DOCUMENTS

| | | | |
|---|---|---|---|
| 5,693,091 A | 12/1997 | Larson, Jr. et al. | |
| 5,810,708 A * | 9/1998 | Woodard ............ | A61M 1/1037 600/16 |
| 2004/0024285 A1* | 2/2004 | Muckter ............... | A61M 1/101 600/16 |
| 2004/0077995 A1* | 4/2004 | Ferek-Petric ........... | A61M 5/14 604/66 |
| 2007/0073393 A1* | 3/2007 | Kung .................... | A61M 1/101 623/3.13 |
| 2012/0078031 A1 | 3/2012 | Burke | |
| 2012/0157753 A1* | 6/2012 | D'Ambrosio ......... | A61M 1/127 600/16 |
| 2012/0310036 A1 | 12/2012 | Peters | |

FOREIGN PATENT DOCUMENTS

| | | |
|---|---|---|
| TR | 2012/09878 | 3/2014 |
| TR | 2012/15023 | 6/2014 |
| WO | WO2012/148367 A2 | 11/2012 |
| WO | WO2013/185073 A1 | 12/2013 |

* cited by examiner

PERMANENT TOTAL ARTIFICIAL HEART DEVICE

TECHNICAL FIELD

The invention is about a permanent total artificial heart device system that is developed for the patients who are at the end-stage heart failure and included in the heart transplantation program, and which is placed into the ventricles of the patient's heart completely or into the pericardium (intrapericardial cavity) surgically placing it into the space obtained when a piece of ventricle is removed while protecting the patient's heart valves and heart conduction system.

PRIOR ART

As it is known, today it is rather difficult to find sufficient number of suitable donor hearts. Therefore, there is no other option than developing total reliable, artificial heart devices. It seems that with the development of these devices, bionic hearts will replace heart transplants from people to people. These devices are the systems of devices comprising of electric motors, batteries, and control units, and are capable of doing all cardiac pump functions and able to provide lifetime sufficient and pulsatile blood flow to patients. Moreover, the system offers a high quality of life to the patients through wireless energy transfer.

Today, tens of thousands of people receive heart failure treatment as a result of coronary heart disease, and heart transplant comes up when drug treatment is insufficient. However, it is not very easy to find a donor for a heart transplant. Approximately 20,000 patients need a donor heart annually in the world, but unfortunately that amount number of heart donors cannot be found. Older systems were designed with an electric motor and it was connected to a snail turbine running with it. There are two artificial vascular input and outputs descending and ascending the system. There have been numerous studies to develop an artificial heart device around the world upto now; Syncardia is a device running with pneumatical system. It has been developed as a device to be used temporarily during the period until which a donor heart is found. The total pneumatic artificial heart system Carpentier developed has not been installed yet. AbioCor is a device designed and developed completely to maintain the body's circulatory system, and clinical trials are ongoing. Compressed air systems have the disadvantages such as running noisily and giving rise to many complications.

Impressive developments have been witnessed in electric motors recently. Due to their high efficiency and producing more power, the use of new generation of brushless electric motors are now widespread in many areas and their yields has reached to 98%. Moreover, new generation of brushless electric motors exhibit excellent power/weight ratio. They have the advantages such as operating quietly, easy maintenance, long lasting, running at high speeds, and producing more torque.

Furthermore, these motors can also be run underwater (therefore also within the human body) if necessary insulation is made at the connection points as these engines have no mechanical contacts. The first motor parts of the brushless motor that wear out are the bearings that support the motor shaft, and the life of porcelain ball bearings developed in recent years has been now much extended. However, if magnetic bearings are used and non-contact rotation is provided instead of using bearings, there will be almost no part of these engines to wear out. Nevertheless, the disadvantages such as complex control systems and overheat of the engine should not be ignored.

On the other hand, the direct drive technology has replaced the conventional engine and transmission systems more often than ever before, and quickly nowadays. In direct drive technology system, mechanical interfaces such as belt systems with various screws, gear boxes have disappeared, and this case increases the efficiency, precision and performance of the system. Also, they are easy to design. All of them can not be realized with conventional drive systems.

The advantages of direct drive technology are as follows: efficiency has increased (motor power is not wasted by friction), lifetime has extended (it also means it has fewer moving parts and has fewer broken parts), noise and vibration has decreased, it has faster and more precise positioning and higher torque capabilities. What determines the overall performance of the system is the unity of all of these elements being together as a whole. This technology is currently used in wind roses, CNC machines, fast trains, and electric and hybrid vehicles, vehicles, in biomedical vehicles, and is rapidly becoming widespread nowadays.

BRIEF DESCRIPTION OF THE INVENTION

The invention is about a permanent total artificial heart system developed for the patients kept in the heart transplant program awaiting a heart donor due to end-stage heart failure. It is placed into the heart with a surgical attempt in the ventricle or a portion of ventricles is removed and is located in place of it. The atrium is not interfered during this process, as well as the patient's aorta and the conduction system of the heart consisting of pulmonary heart valves, the sinus node, the atrioventricular node and the ways of conduction are protected. Thus, patients will continue their lives smoothly with their own heart valves and with the natural rhythm of their own hearts instead of the prosthetic valves.

The electrical system that runs the heart is called "the heart's conduction system". The conduction system of the heart consists of sinus node, the atrioventricular node and the ways of conduction, and the rhythm of the heart produced by the system is called"sinus rhythm". Since the conduction system of the heart is not damaged during the placement of the artificial heart, sinus node will continue to produce ECG signals, and these signals will be detected by the artificial heart system and pulsatile blood flow will be achieved by starting and stopping pump blood with normal sinus rhythm. In other words, the artificial heart will not controlled by its own microprocessor but by the patient's sinus node, so that the patients will continue their lives with the natural sinus rhythm of their own hearts, and the cardiac rhythm will accelerate while expending energy and slow down while resting.

This device runs with specially designed engines, and can fulfill all the heart pump functions for many years. The motors include rotors rotating on a bed of magnetic bed, but without a rotation pin, and helical vanes built into the rotor provide non-pulsatile blood flow. This high quality device which will provide a patient a high quality of life with wireless energy transfer is a new generation permanent total artificial heart device unifying the advantages of direct drive technology with all the advantages of brushless electric motors.

The motors we used in a total artificial heart device are brushless electric motors running synchronous or asynchronous with either true or alternating current, and direct drive technology has been used. Besides, rotors of the motors are hollow and there are helical vanes integrated with the rotor, as well as no pin, and this is the basis of our invention.

When the direct drive technology we employed is installed into the total artificial heart device, it will provide grave advantages. Perhaps, heart transplant from person to person will be no longer required in the near future with the development of this system, and "permanent" total artificial heart devices will take its place.

THE EXPLANATION OF THE FIGURES

FIG. 1. Total Artificial Heart Device
FIG. 2. General View of Left and Right Ventricle Motors
FIG. 3. Detailed View of Ventricular Engine
FIG. 4. Cross-sectional View
FIG. 5. Cross Sectional View Inserted into the Pulmonary Artery
FIG. 6. Cross Sectional View Inserted into the Aorta
FIG. 7. Control Flow Chart
FIG. 8. The View of Exterior Apparatus
FIG. 9. The View of Interior Apparatus The provisions of the part numbers used in figures are given below;
1. Total Artificial Heart Device
1.1. Left Ventricle Motors
1.2. Right Ventricle Motors
1.3. Left Atrium Inflow Tractus
1.4. Right Atrium Inflow Tract
1.5. Ascending Aorta
1.6. Main Pulmonary Artery
1.7. Aortic Valve
1.8. Pulmonary Valve
1.9. Spacer Apparatus
2. Interior apparatus
2.1. Interior Control Unit
2.2. Internal Battery
2.3. Internal Power Transmission Apparatus
2.4. Protective Cover
2.5. Electrical Power Cable
2.6. Microprocessor
2.7. Blood Pressure Sensor
2.8. Blood Flow Sensor
2.9. Motor Driver Circuit
3. External Apparatus
3.1. External Control Unit
3.2. External Battery
3.3. External Power Transmission Apparatus
3.4. Touch Screen
3.5. Buzzer with Light
4. Adapter

DETAILED DESCRIPTION OF THE INVENTION

Total artificial heart device (1) mainly consists of internal apparatus (2), external apparatus (3) and adapter (4) fragments. Total artificial heart device (1) is composed of the left ventricle engine (1.1), the right ventricle engine (1.2), left atrium entrance way (1.3), right atrium inflow tract (1.4), aortic outflow tract (1.5), and pulmonary arterial outflow tract (1.6), aortic valve (1.7), and pulmonary valve (1.8), spacer apparatus (1.9) of parts. Interior apparatus (2) the internal control system (2.1), the internal battery (2.2), internal power transfer apparatus (2.3), the protective sheath (2.4), the electrical power cord (2.5), microprocessor (2.6), blood pressure sensor (2.7), blood flow rate sensor (2.8) and the motor driver circuit (2.9) fragments. External apparatus (3) consist of the external control unit (3.1), external battery (3.2), the external power transfer apparatus (3.3), touch screen (3.4) and the light and the buzzer (3.5) parts.

The engine designs of our heart assist devices, mentioned in the national patent applications we had done before with the reference numbers TR2012/00951, TR2012/07222, TR2012/09878, TR2012/15023 and the patent applications we had applied under the Patent Cooperation Treaty regulations with the reference number PCT/TR2012/00055, have also been employed in the engine designs of the total artificial heart.

Direct drive technology is now replacing the conventional engine and transmission systems. Various screws, belt systems, gear boxes and mechanical interfaces are removed in the direct drive technology systems, and these have increased the efficiency, accuracy and performance of the system. Moreover, they are easy to designs, and it is impossible to realize all of them with conventional drive systems. To name a few benefits of this technology; productivity has increased (engine power is not wasted by friction), lifetime has extended (having fewer moving parts), noise and vibration have decreased, they have more rapid and precise positioning and high torque capabilities.

Figure 1:
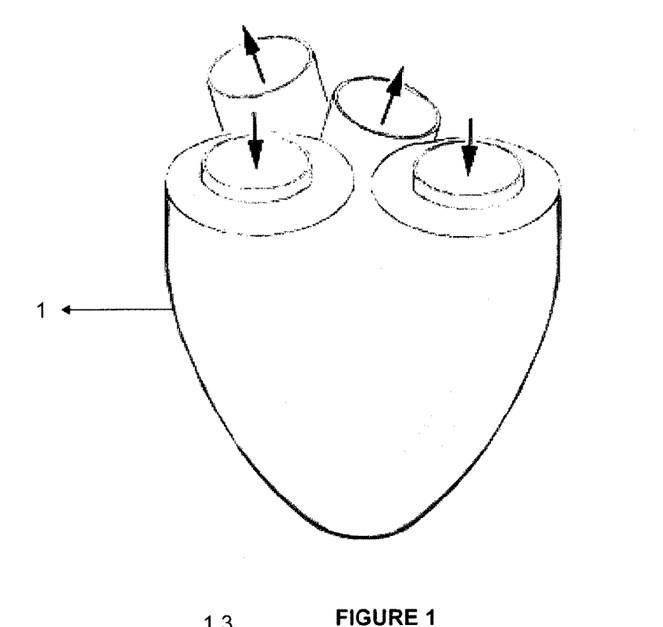
Figure 2:
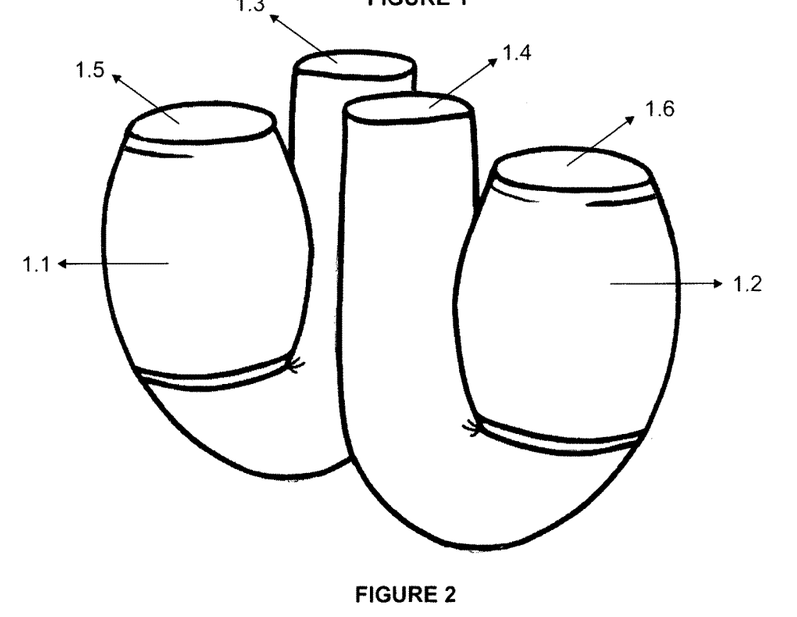
Figure 3:
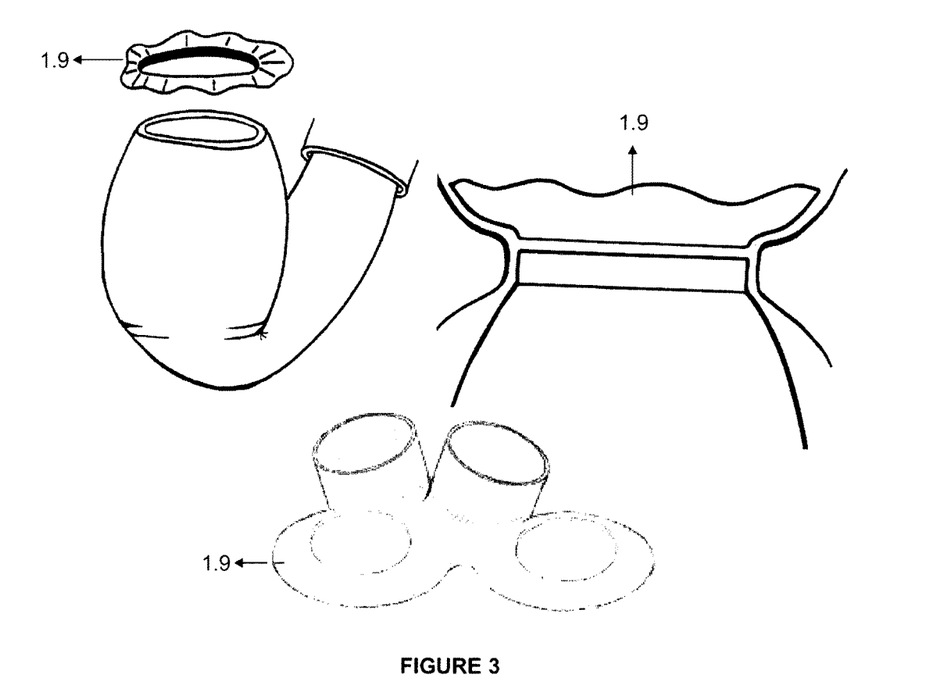
Figure 4:
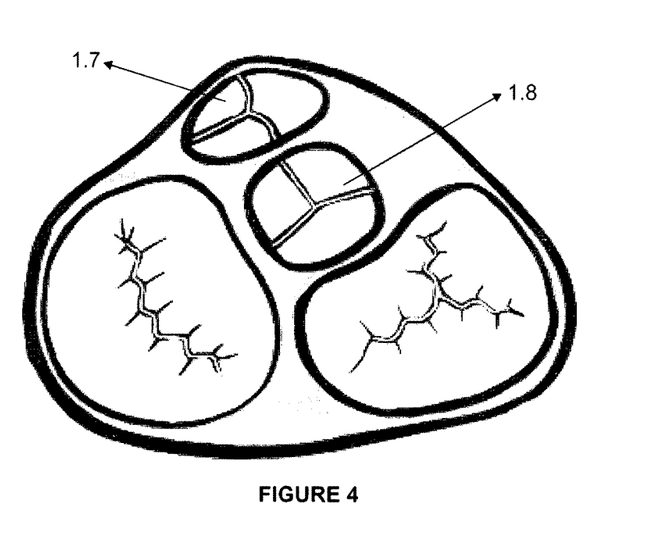

All of these elements determining the overall performance of the system create a unity. This technology has been employed in our total artificial heart device (1). Total artificial heart device (1) includes neither a left (1.1) and a right ventricular engine (1.2) nor the intermediate elements and a rotor with a pivot pin. The left ventricle engine (1.1) and the right ventricle engine (1.2) have the ability to transmit the power from the rotor to the system directly without any connecting link components. There will be design options of various sizes (pediatric and even neonatal models) of the precise engines with long life that will not wear out over time.

There are high sensitivity of blood pressure and blood flow rate sensors (2.8) in the left ventricular engine (1.1) and the right ventricle motor (1.2) of our total artificial heart device (1), and these sensors (2.8) provide feedback to the microprocessor (2.6). This state is required for the optimum performance of the total artificial heart device (1). Since the magnetic bearings provide rotation to the rotor without friction, there will be no wear out or component aging, and this will enhance the long life of the total artificial heart (1).

A healthy human heart has a pulsatile blood flow with the contraction and relaxation of the ventricles (systole and diastole). The perfusion provided with pulsatile blood flow has hemodynamic significant advantages when compared with non-pulsatile perfusion. Pulsatile blood flow is a physiological blood flow pattern in a healthy person. Pulsatile blood flow in the patient's bloodstream means an additional of energy transfer into the micro-circulation, and this extra kinetic energy helps red blood cells transport to capillary vessels. Thus, it increases capillary circulation, helps lymph circulation, and ultimately, it has a positive effect on the cell metabolism. A good total artificial heart device (1) should ensure pulsatile blood flow with natural intermittents to the human body as it has accustomed to.

In our device, the left ventricle engine (1.1) and the right ventricle engine (1.2) run making stop-and-go, and they start during the systole and stop during the diastole period. Systolic and diastolic interval time is constantly changing in a healthy subject. The duration of systole is the contraction time of the heart (systolic ejection time). The blood flow is adjusted according to the needs of the body by extending or shortening the period. Systolic ejection time intervals increase when blood flow is required to increase, and Systolic ejection time intervals decrease when it is necessary to reduce blood flow. This is provided by the heart's own natural sinus rhythm. As our invention will run with ECG signals synchronously, it will keep up with the sinus rhythm of the heart, and systolic time will extend or shorten continuously according to the requirement of blood flow.

Microprocessor will undertake this job in the patients, whose heart conduction system damaged or out of work, with the help of software which contains similar algorithms. Moreover, the software includes algorithms that will initiate the microprocessor immediately when a technical problem occurs in the records of the ECG signal.

Figure 5:
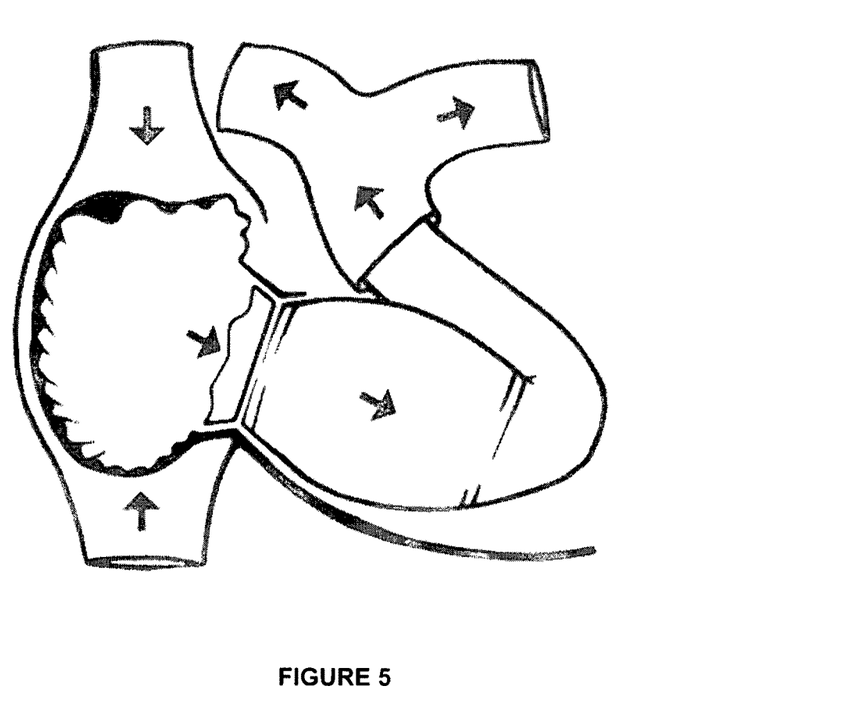
Figure 6:
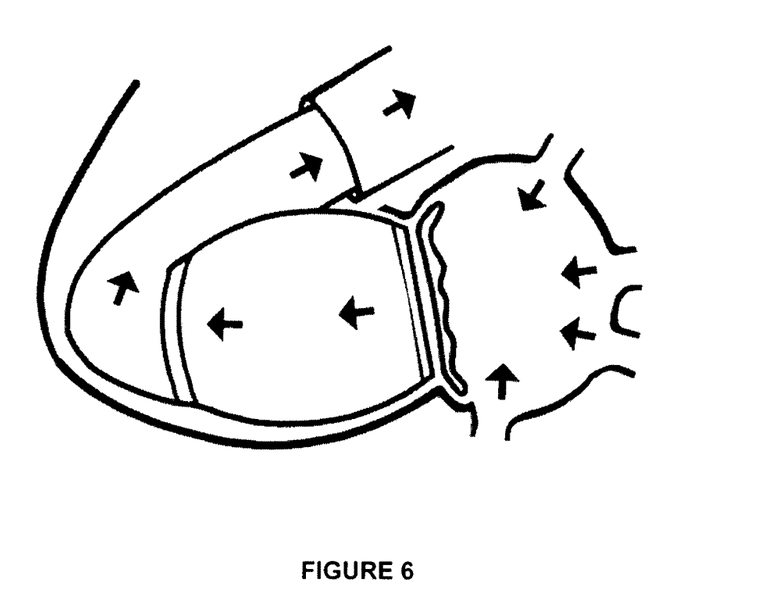

A one-way valve in the aorta outflow tract (1.5) and the pulmonary arterial outflow tract (1.6), and an artificial aortic valve (1.7) on aorta, and an artificial pulmonary valve on the pulmonary artery (1.8) are available. These valves open fully during the systole and close during diastole to prevent back flowing of the blood.

Artificial aortic and pulmonary valves have artificial joints apparatus that are easily removable, and they can be removed and fitted easily on demand one by one or the other or both.
If the patient's own aortic and pulmonary valves of heart are healthy and functioning properly, artificial aortic and/or pulmonary heart valves will be removed, and while artificial heart is being positioned in its place without damaging these valves so that the system can use the patient's own natural heart valves.

Total artificial heart device (1) has the parts to be attached to the patient such as the left atrium entrance way (1.3), the right atrium entrance way (1.4), aortic outflow tract (1.5), and pulmonary arterial outflow tract (1.6). The connection will be achieved by placing it into the lining of the heart instead of a portion of the heart's ventricles extracted from patients with open-heart surgery. Not all of the heart but only a part of the ventricles of the heart is removed during surgery, and atriums, sinus node, atrioventricular node conduction pathways of the heart are not disturbed.

Figure 7:
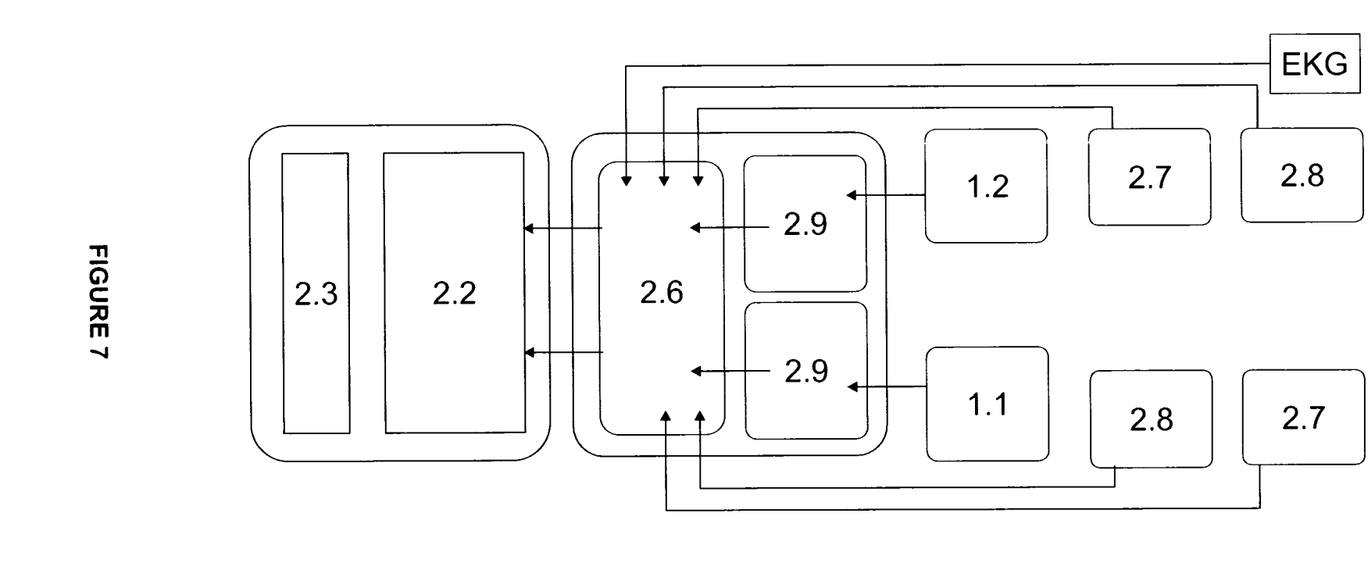
Figure 9:
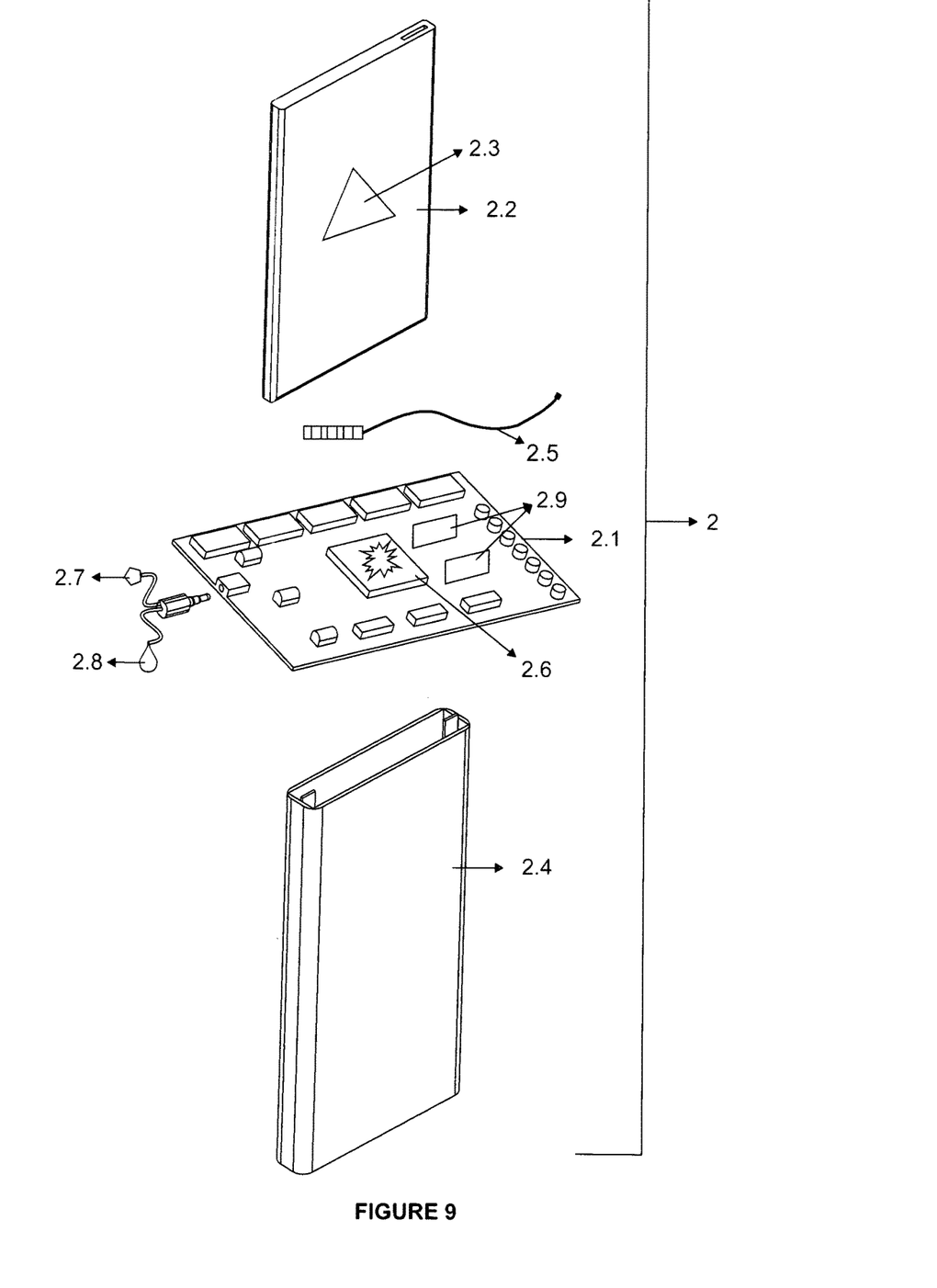

Internal control system (2.1) receives the data of the aorta and pulmonary artery blood pressure and blood flow from the blood pressure sensors (2.7) and blood flow sensors (2.8), and processes them in real-time with the help of microprocessor, suitable software and algorithms. The speed of the motors per minute in the left ventricle (1.1) and the right ventricle (1.2) and/or duration of systole are adjusted according to the data obtained from these sensors and algorithm. When the blood pressure goes up above a certain limit, the engine slows down and/or systolic time intervals shortens, and when the blood pressure falls below a certain limit, the engine accelerates and extends the systolic time intervals, thus the formation of normal pulsatile blood flow closest to the heart's is provided.

Figure 8:
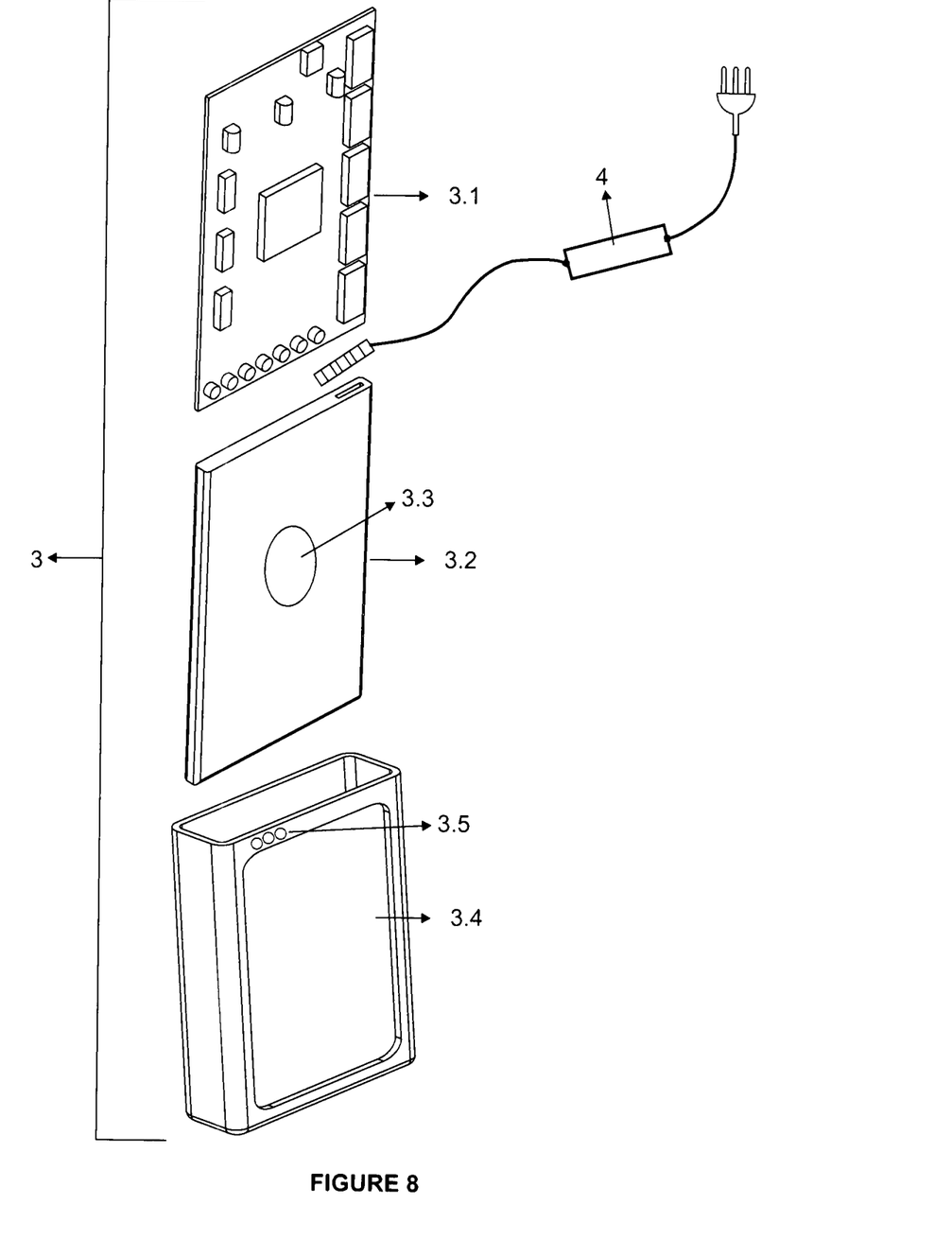

As the total artificial heart device (1) can be produced in small volumes, it can be applied to all patients, including pediatric and newborn babies. The device has two batteries; an internal battery (2.2) and an external battery (3.2). The apparatus (3) in which external battery (3.2) is located can be recharged with its own adapter (4).

External apparatus (3) has three separate parts each of which have different functions. The first equipment is a rechargeable lithium-ion battery. This external battery (3.2) is an electrical energy store that provides the necessary energy. The second equipment is the internal battery (2.2) that is power transmission apparatus (3.3). The third is the external control unit (3.1). The external control unit (3.1), continuously updates the vital data such as the charge status of the internal battery (2.2), blood pressure, blood flow and heart rate in real time thanks to a remote control system, and shows on the touch screen (3.4) when prompted. Thus, one side of external apparatus (3) is made up of the touch screen (3.4) of the control unit (3.1) and the other side is the induction surface of external power transmission apparatus (3.3).

Internal battery (2.2) and the internal control system (2.1) are placed into a protective cover (2.4) both as integrated (monolithic). The cover is made of a biocompatible material. Internal control unit (2.1) settings can be changed from the touch screen (3.4) of the external control unit (3.1) after the authorized user's input.

The power from the external battery (3.2) is transmitted to the internal battery (2.2) located under the skin with the help of a wireless technology. This transmission is achieved through induction current, and there is an internal power transmission apparatus in the a system placed under the skin by a cardiac surgeon, and an external power transmission apparatus on the other is outside of it. Induction current produced by the external apparatus is picked up by the internal apparatus, and is converted to alternating current, and then it is stored into the battery being converted into the direct current.

Internal battery (2.2) and the external battery (3.2) are formed when the lithium-ion battery cells are linked together. Lithium-ion batteries include lithium and polymer chemicals in their structures, and today they are widely used in the model aircraft, navigation devices, mp3 players and mobile phones. Lithium-ion batteries are made up of cells. The nominal voltage of each cell is 3.7 volts, and these cells can produce batteries whose values increase at 3.7 volt and its folds with serial or parallel connections. Although lithium-ion batteries are quite lighter than NiCd and NiMH batteries, they can store more energy, and have also longer battery life.

There is a microprocessor (2.6) in the internal control unit (2.1), and its system settings can be reset from the touch screen (3.4) of the external control unit (3.1) after the authorized user's input.

The left ventricle engine (1.1) and the right ventricle engine (1.2) are brushless motors. Synchronous, servo or asynchronous motor types can be employed. As it is known, a microprocessor is required to run these advanced brushless motors. The microprocessor in the internal control unit (2.1) performs this task. Microprocessor engines control in a detailed manner, amplify the signals from the sensors through the amplifier (amplifier) circuit, and analyze with the help of the software by means of a suitable algorithm prepared and through the ADC (Analog-Converter to Digital), and implement in real-time.

A microprocessor (2.6) controls synchronized both of the right ventricle engine (1.2) and the left ventricular engines (1.1) per minute (rotation/minute) revolution speed led by a software setting. While blood pumps run intermittently, start and stop time intervals occur, and this gives rise to pulsatile blood flow. From a physiological point of view, for example, when a person is in any effort, the human body responds that by increasing pulse rate per minute. A reverse situation occurs at rest, and the number of pulses is at the lowest level. Another rule is that the duration of systole increases when the cardiac output increases. Conversely, systolic interval decreases when cardiac output decreases. The duration of systole and diastole of a healthy human heart, especially, the systolic ejection time can be measured in milliseconds echocardiographic examinations, and the duration of systole is approximately half of the diastole time. Also, the coordination between the systolic and diastolic time intervals of the total artificial heart should be as in a healthy human. Thus, the total blood flow is obtained, and as the systolic time intervals increases, the blood flow increases, and when the systolic time intervals decreases, blood flow decreases.

Only the ventricles of the heart is removed from the patient at the surgery, and the heart's sinus node and the atrioventricular node and nerve conduction paths will remain and run intact. Therefore, the right atrial sinus node will continue to produce ECG signals. When the total artificial heart runs synchronous with the ECG signals, it will act in accordance with the running physiology of a healthy human heart.

Initially, the systolic period of artificial heart will be half as much as diastolic time, but with the efforts of the patient, ECG signals caused by the sinus node will begin to occur more frequently. Microprocessor will respond by extending the duration of systole when the ECG signals become frequent, thus, the blood flow increases as the patient makes efforts. A reverse situation will occur when the patient is at rest.

The blood flow passing from the aorta is equal to the flow from the pulmonary artery in a healthy person. That is, the ratio of mean pulmonary blood flow (Qp) to systemic blood flow (Qs) always equals to one (Qp/Qs=1). Microprocessor will always keep the Qp/Qs=1 equation uninterrupted after processing the data separately from the blood flow meter on the aorta and pulmonary artery; if blood flow increases in one the artery, the microprocessor will shorten the duration of systolic blood flow of that blood pump motor, and extend the systolic time interval if blood flow decreases. Thus, the microprocessor runs two blood pump motors separately.

The surfaces of the left ventricle engine (1.1) and the right ventricle engine (1.2), which may contact with blood and body tissues, will be covered with special materials such as nickel-titanium alloy and porcelain to which human body will not react, and the electrical components will be isolated from the blood.

Assuming that electric motors get heated while running under high performance, the outer surface of the artificial heart that will be placed into the pericardial cavity will also be insulated. This insulation, as in the steel thermos containers, will be carried out by vacuuming the air in the gaps, and the gaps that cannot be vacuumed will be insulated with porcelain-like materials that have both heat and electrical insulation properties. In addition, the system will operate more stable as both blood pump motor will turn in the opposite directions to each other.

The upper and lower speed limits of the heart engines will be determined and set either automatically or manually by the patient's physician according to the conditions compatible with the patient's age, weight, and specific health conditions.

When a donor's heart is transplanted to the patient, immunotherapy (a drug treatment that prevents the rejection of the donor heart by suppressing the immune system) is administrated, and this drug therapy will be out of question for the patients with total artificial heart transplantation.
In addition, some heart diseases may lead to heart failure even in newborn infants, and therefore, artificial heart devices can be produced in all sizes, including newborn infant sizes.

When exceptional cardiac malformations occur in cases, prototype molds will be prepared from three-dimensional patient's heart MR or CT images obtained by imaging and a patient-specific total artificial heart device compatible with the morphological structure of the patient's heart will be produced if required.

Since the total artificial heart device is vital for the patient, all software, hardware, apparatus and all functions of the system will have a standby backup, and will have master and apprentice or master/slave configuration, and they will be designed so that when one fails, the other can be activated instantly.
In order to prevent the damage of electrical leakage and high temperatures that may arise when total artificial heart device runs, all around the system will be coated with a biocompatible insulating material that enhances electrical and thermal insulation.

One of the properties of total artificial heart device is that when a donor's heart is found, it makes it possible to remove the artificial heart installed without damaging the anatomical structures surrounding heart.
Another feature of the total artificial heart device is the spacer (connector) that has been developed to help the cardiac surgeon while installing it into the patient. This median apparatus is made of biocompatible material, and it is a spacer (connector) compatible with mitral and tricuspid valve inputs and aorta and pulmonary arterial outputs after the removal of both the right and left ventricles of the heart. A surgeon first adapts this spacer (connector) to the output and input tracks of the heart with a surgical intervention and sutures it, and after this process, she takes the actual total artificial heart device and fastens it to spacer (connector) with a simple mechanical process.

After all these, one of the most vital tasks before the artificial heart device operates is to ensure that there is no air embolism. An important task before running the artificial heart is that all the entire interior apparatus, including power transmission apparatus must be located and all connections must be done.

When myocardium loses its contractility feature almost completely, artificial heart components can be placed separately into the right and left ventricles without interference the heart muscle. The artificial heart component located in the right ventricle of a heart includes a heart assist device, and takes the blood from the right atrium and passes it into the pulmonary artery. The artificial heart component located in the left ventricle also includes a heart assist device, and it takes the blood from the left atrium and passes it into the aorta. Both heart assist devices are controlled by a common microprocessor.
As the devices are located into the ventricles, this kind of structure can be called as "in ventricular heart assist device" (intraventricular heart assist device). In this case, without ventriculotomy, the components of both heart assist devices can be placed into the ventricles through mitral and tricuspid valve caps with a simple atrial incision.

Thermal insulation will be carried out assuming that total artificial heart device will overheat, and damage the surrounding tissues and organs while running. For this purpose, it contains spaces providing heat insulation with the similar logic as in the air in the thermos containers whose air is vacuumed. Thus, the lightest method will be used for the thermal insulation while the patient's body is not loaded with unnecessary material or metals.

While a total artificial heart device is being installed into a patient by a heart surgeon, there will be a spacer (connector) (1.9) made of biocompatible material which will make the surgical procedures easy. First, the surgeon will locate this apparatus into the heart and the circulatory system of the patient, and then will install easily the main part of the artificial heart to this apparatus (1.9) mechanically (by fastening, attaching to each other by means of permanent magnets, or screwing with the help of screws).

The microprocessor (2.6) of artificial heart will produce light and acoustic warnings (3.5) in such cases of emergency as when the internal and external battery charges are within the danger limits of pre-determined limits or there is abnormal increase or decrease in the blood flow rate or blood pressure, and thus, patients and their relatives will be warned beforehand. Moreover, when the the data reaches the danger limit, all the people will be informed as it includes a software that sends messages to the patient's physician, hospital or ambulance service or predetermined addresses.

The external control unit (3.1) of the artificial heart includes a clock, a calendar and software that display the current screen values and the coordinates where the patient is. In the event of any negative case, the software will notify the relevant places the pre-determined coordinates where the patient is via SMS or e-mail. For this purpose, the system includes a modem that provides wireless internet access. It also includes a software that allows the the patient's physician to reset the control unit by providing a remote access via the internet being entered by an authorized user.

In order not to disturb the patient when its engines start and stop, the outer part of the artificial heart will be coated with a biocompatible silicone-like material that dampens vibrations.

What is claimed is:

1. A total artificial heart device for patients with end-stage heart failure and insolvent heart patients, comprising at least two blood pump motors that run synchronously with a sinus rhythm of a sinus node of a heart of a patient and can be controlled individually;
    wherein one of the blood pump motors is a left ventricle blood pump motor, and the other is a right ventricle blood pump motor;
    wherein the left ventricular blood pump motor maintains microcirculation by pushing blood from the right atrium into a pulmonary artery direction;
    wherein the right ventricular blood pump motor maintains systemic circulation by pushing blood from the left atrium into an aorta direction;
    wherein the total artificial heart device is configured to be placed into a heart membrane of the heart by removing left and right ventricles of the heart surgically, and alone provides a blood flow required for the patient;
    wherein the total artificial heart device further comprises an internal control unit, which comprises a microprocessor that controls the left ventricular blood pump motor and the right ventricle blood pump motor synchronously to keep aorta blood flow rate and pulmonary arterial blood flow rate constantly equal in real time and uninterrupted;
    wherein the total artificial heart device further comprises a first annular spacer and a second annular spacer, an upper end of the left ventricular blood pump motor is installed to the first annular spacer, and an upper end of the right ventricular blood pump motor is installed to the second annular spacer.

2. The total artificial heart device of claim 1, further comprising:
    an internal battery which provides energy to the blood pump motors;
    an external battery that supplies wireless energy to the internal battery; and
    an internal power transfer apparatus that can transfer energy between both internal and external battery and an external power transmission apparatus.

3. The total artificial heart device of claim 1, further comprising total four vessel connections: a left-ventricular inlet passage, a right ventricular inlet passage, an aortic outflow tract and a pulmonary arterial outflow tract.

4. The total artificial heart device of claim 1, wherein the left ventricular blood pump motor and the right ventricle blood pump motor are the parts enabling a system to run stable by turning in the opposite directions of each other;
    wherein the left ventricular blood pump motor further comprises a rotor rotating stably in a stator with the help of a magnetic bearing;
    wherein the rotor is in a form of squirrel-cage structure made from a plurality of metal bars and a plurality of short-circuit rings with high electric conductivity;
    wherein all inner and outer surfaces of the left ventricular blood pump motor and the right ventricle blood pump motor have been coated with a biocompatible material.

5. The total artificial heart device of claim 1, further comprising an artificial aortic valve and an artificial pulmonary valve on ascending aorta route and pulmonary artery route, respectively.

6. The total artificial heart device of claim 1, wherein the first annular spacer and the second annular spacer make it possible to install the total artificial heart device without damaging the heart's own aorta, pulmonary artery and heart muscles.

7. The total artificial heart device of claim 4,
    wherein an inner part of the rotor is empty;
    wherein the rotor forms and turns with a unity with a plurality of helical vanes placed inside;
    wherein the rotor provides sufficient blood flow to the patient pushing the blood back to front;
    wherein the rotor has no pin while rotating freely.

8. The total artificial heart device of claim 2, wherein the microprocessor processes a plurality of blood flow data synchronously coming from an aorta and a pulmonary artery of the patient to control the aorta blood flow rate and the pulmonary arterial blood flow rate.

9. The total artificial heart device of claim 2, wherein the internal control unit provides a plurality of data transferred between the internal control unit and an external control unit wirelessly.

10. The total artificial heart device of claim 2, wherein the external power transmission apparatus provides wireless charging to the internal battery from the external battery through a plurality of induction currents.

11. The total artificial heart device of claim 2, wherein the internal battery and the internal control unit are configured to be placed into the patient's body in a protective sheath made of an alloy or a material to which human body does not react.

12. The total artificial heart device of claim 2, further comprising an external apparatus which displays information in the internal and external control unit, internal and external battery charge status in real time on a touch screen;
    wherein the touch screen makes it possible for an authorized user to service all the setting up a system on the touch screen.

13. The total artificial heart device of claim 8, wherein the microprocessor gives a plurality of light and acoustic warnings in such cases of emergency as when the internal and external battery charges are within a plurality of danger limits or there is an abnormal increase or decrease in the blood flow rate or blood pressure;
    wherein the microprocessor has a software that sends messages to the patient's physician, hospital or ambulance service or predetermined addresses, when the data reaches a danger limit;

wherein the microprocessor adjusts the blood flow by extending or shortening the duration of systole synchronous with a plurality of ECG signals caused by the heart's own sinus node;

wherein the microprocessor processes the blood flow data received separately from blood flow meters on the aorta and the pulmonary artery to keep a ratio of mean pulmonary blood flow to systemic blood flow always necessary for the patient according processing the ECG signals and collected data together with algorithms.

14. The total artificial heart device of claim 1, further comprising an external control unit which comprises a clock, a calendar and a plurality of coordinates of the patient;

wherein the external control unit is configured to display a plurality of current screen values;

wherein the external control unit is configured to receive settings through remote access on internet entered by an authorized user.

15. The total artificial heart device of claim 14, wherein the external control unit comprises a modem that enables wireless internet access for remote access and monitoring.

16. The total artificial heart device of claim 1, wherein all around of the total artificial heart device is coated with a biocompatible insulating material that enhances electrical and thermal insulation to prevent the damage of electrical leakage and high temperatures that may arise when the total artificial heart device runs, wherein an outer part of the total artificial heart device is coated with a biocompatible material that dampens vibrations in order not to disturb the patient when the motors run.

17. A total artificial heart device for patients with end-stage heart failure and insolvent heart patients, comprising at least two blood pump motors that run synchronously with a sinus rhythm of a sinus node of a heart of a patient and can be controlled individually;

wherein one of the blood pump motors is a left ventricle blood pump motor, and the other is a right ventricle blood pump motor;

wherein the left ventricular blood pump motor maintains microcirculation by pushing blood from the right atrium into a pulmonary artery direction;

wherein the right ventricular blood pump motor maintains systemic circulation by pushing blood from the left atrium into an aorta direction;

wherein the total artificial heart device is configured to be placed into right and left ventricles separately without disturbing heart muscles and alone provides a blood flow required for the patient;

wherein the total artificial heart device further comprises an internal control unit, which comprises a microprocessor that controls the left ventricular blood pump motor and the right ventricle blood pump motor synchronously to keep aorta blood flow rate and pulmonary arterial blood flow rate constantly equal in real time and uninterrupted;

wherein the total artificial heart device further comprises a first annular spacer and a second annular spacer, an upper end of the left ventricular blood pump motor is installed to the first annular spacer, and an upper end of the right ventricular blood pump motor is installed to the second annular spacer.

18. The total artificial heart device of claim 1, wherein the total artificial heart device contains a material that provides both thermal and electrical insulation.

19. The total artificial heart device of claim 1, further comprises an internal battery, an external battery, and an internal power transmission apparatus and an external power transmission apparatus that provide wireless energy transfer.

20. The total artificial heart device of claim 1, wherein the left ventricular blood pump motor and the right ventricular blood pump motor are covered with nickel-titanium alloy or porcelain.

21. The total artificial heart device of claim 1, wherein the left ventricular blood pump motor and the first annular spacer are attached to each other by permanent magnets or screws, and the right ventricular blood pump motor and the second annular spacer are attached to each other by permanent magnets or screws.

22. The total artificial heart device of claim 17, wherein the left ventricular blood pump motor and the right ventricular blood pump motor are covered with nickel-titanium alloy or porcelain.

23. The total artificial heart device of claim 17, wherein the left ventricular blood pump motor and the first annular spacer are attached to each other by permanent magnets or screws, and the right ventricular blood pump motor and the second annular spacer are attached to each other by permanent magnets or screws.

24. The total artificial heart device of claim 17, wherein the total artificial heart device contains a material that provides both thermal and electrical insulation.

* * * * *